US007041985B1

United States Patent
Wang et al.

(10) Patent No.: US 7,041,985 B1
(45) Date of Patent: May 9, 2006

(54) MANIPULATOR FOR MICROSCOPY SAMPLE PREPARATION AND METHODS FOR MAKING AND USE THEREOF

(75) Inventors: Haifeng Wang, Mountain View, CA (US); Loc Vinh, Fremont, CA (US)

(73) Assignee: Western Digital (Fremont), Inc., Fremont, CA (US)

( * ) Notice: Subject to any disclaimer, the term of this patent is extended or adjusted under 35 U.S.C. 154(b) by 0 days.

(21) Appl. No.: 10/986,631

(22) Filed: Nov. 12, 2004

(51) Int. Cl.
*G21K 5/10* (2006.01)
(52) U.S. Cl. .................................. 250/442.11
(58) Field of Classification Search ............ 250/442.11
See application file for complete search history.

(56) References Cited

U.S. PATENT DOCUMENTS

| | | | |
|---|---|---|---|
| 4,793,674 A * | 12/1988 | Buzzio et al. ................. | 385/51 |
| 6,072,157 A * | 6/2000 | Klebanoff et al. ........... | 219/228 |
| 6,891,170 B1 * | 5/2005 | Yu et al. ................ | 250/442.11 |
| 6,911,349 B1 * | 6/2005 | Li et al. ....................... | 438/16 |

OTHER PUBLICATIONS

Declaration of Haifeng Wang Under 37 C.F.R. § 1.56(a), dated Nov. 1, 2004, 2 pages.

* cited by examiner

*Primary Examiner*—John R. Lee
*Assistant Examiner*—Jennifer Yantomo
(74) *Attorney, Agent, or Firm*—Carr & Ferrell LLP; Joshua C. Harrison, Esq.

(57) ABSTRACT

Manipulators for handling micron-scale samples, methods for making probes for the manipulators, and methods for using the manipulators are provided. An exemplary manipulator includes a probe, a probe holder, and a mechanical positioner. The probe includes an electrically conductive surface, a proximal end and a distal end where the distal end has a truncated conical shape with a generally flat face, and a bore extending from the proximal end to the face. The probe holder engages the proximal end and includes an inlet in fluid communication with the bore and with a source of sub-ambient pressure. An exemplary microscopy inspection method includes forming a free-standing membrane, positioning the probe of the manipulator proximate to the membrane, drawing the membrane to the face by drawing a vacuum through the bore, placing the membrane on a sample support, and inspecting the membrane with a microscope.

20 Claims, 8 Drawing Sheets

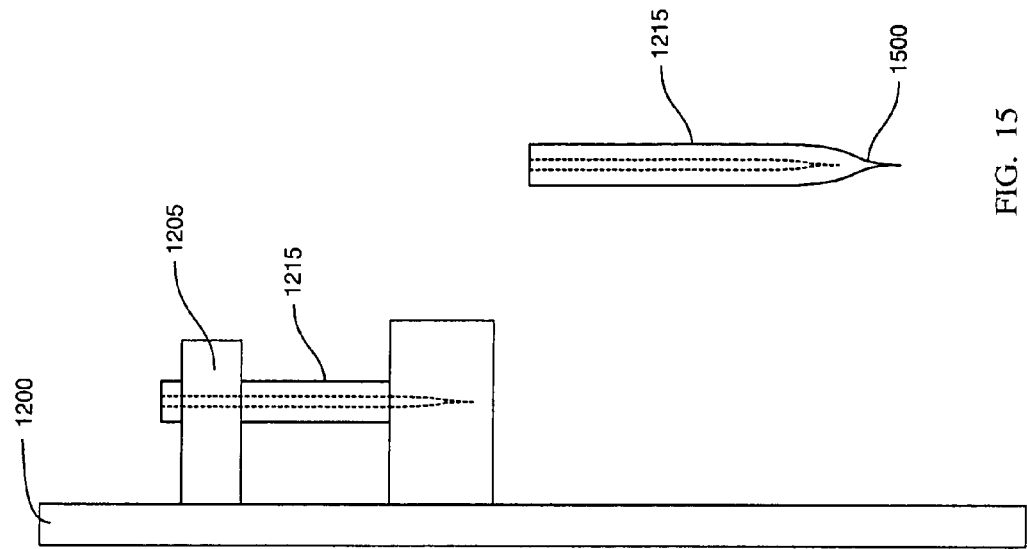
FIG. 15
FIG. 14
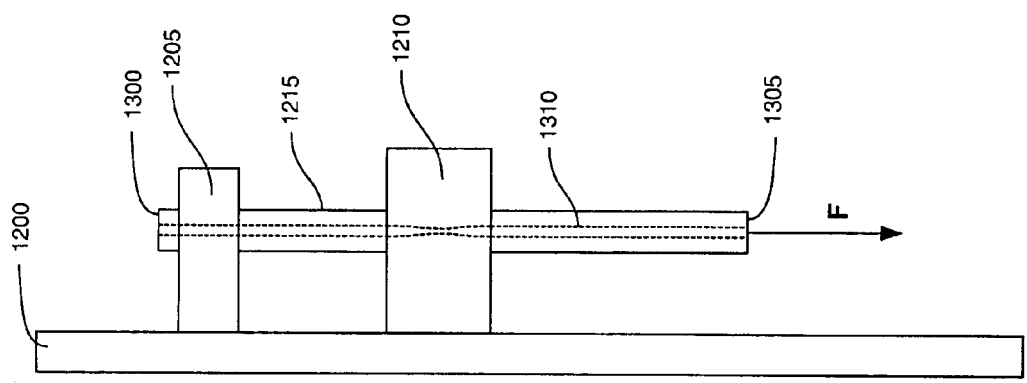
FIG. 13
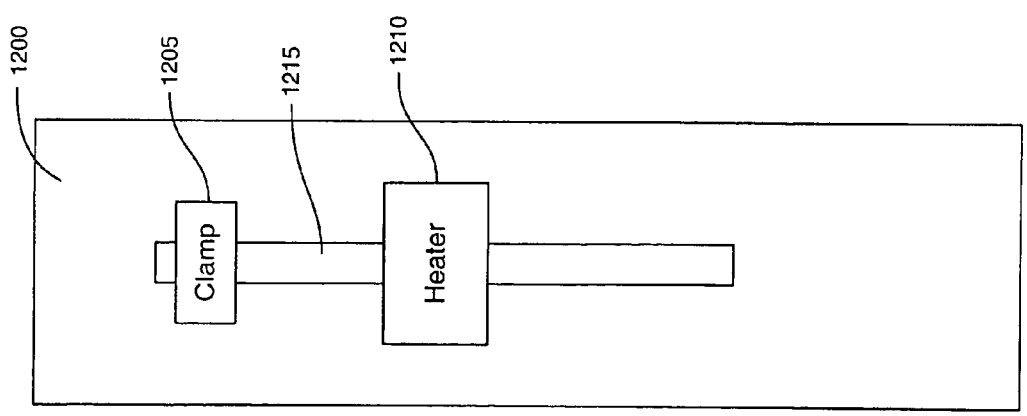
FIG. 12

MANIPULATOR FOR MICROSCOPY SAMPLE PREPARATION AND METHODS FOR MAKING AND USE THEREOF

BACKGROUND OF THE INVENTION

1. Field of the Invention

The disclosure relates generally to the field of device inspection by electron microscopy, and more particularly to handling samples made for such inspection.

2. Description of the Prior Art

Various devices, such as semiconductor products and disk drive transducers, comprise features that are fabricated at micron and smaller scales. For quality assurance and trouble-shooting purposes, it is often necessary to inspect certain features of such devices at different stages in the manufacturing process. Electron microscopy is a common tool for such inspections. Scanning electron microscopy (SEM) creates images by scanning an electron beam across a surface and measuring the electrons that are reflected towards an electron detector from features on the surface. Another technique, transmission electron microscopy (TEM), creates images by shining an electron beam on a very thin film and detecting those electrons that pass through the film. Features in the film interact with the electrons differently than the surrounding material, thus creating contrast in the resulting image. Although TEM typically provides greater spatial resolution than SEM, it will be appreciated that TEM requires highly specialized sample preparation to produce very thin films around the particular micron-scale and smaller features of interest. Such sample preparation is typically destructive to the device being inspected. The burden of sample preparation has kept TEM from being more widely accepted for routine inspections.

Existing techniques for TEM sample preparation in the field of device inspection employ focused ion beam (FIB) milling and are either in-situ or ex-situ. In-situ techniques produce the sample entirely within a FIB system, while ex-situ techniques complete the sample preparation outside of the FIB system. FIGS. 1–3 show the basic steps common to both sample preparation methods. FIG. 1 shows an initial device 100 having a feature of interest buried within at a reasonably well understood location.

In FIG. 2 a first pit 200 is milled into the device 100 on one side of the feature of interest. Next, a second pit 205 is milled into the device 100 on the other side of the feature of interest. Either of the first or second pits 200 or 205 is carefully enlarged in the direction of the other until only a very thin membrane 210 containing the feature of interest remains between the pits 200, 205.

As shown in FIG. 3, which shows the membrane 210 from the perspective of the section 3—3 of FIG. 2, a further thinned central portion 300 of the membrane 210 that includes the feature of interest can be created by additional FIB milling, leaving somewhat thicker side portions 305 for structural integrity on either side of the central portion 300. Next, the FIB system is used to cut the membrane 210 from the surrounding material, much like a welder's torch but on a much finer scale, to allow the membrane 210 to be free-standing. After a cut 310 is completed, the membrane 210 is held in place only by static electricity. The free-standing membrane 210 thus formed typically has dimensions of about 5 µm×15 µm. The central portion 300 is typically thinned to a thickness of about 100 nm or less, while the thickness of the side portions 305 is on the order of about 500 nm.

In the in-situ method, a very fine probe is first brought into contact with one of the side portions 305. Next, a film of platinum is deposited over the membrane 210 and the probe until the thickness of the platinum is sufficient to essentially weld the two together. The membrane 210 can then be lifted away from the device 100 and transferred to a specialized sample grid for TEM microscopy.

A disadvantage of the in-situ technique is that the membrane 210 must be cut from the probe by further milling. Additionally, the film of platinum must be cleaned from the surface of the membrane 210 by still further milling. Besides possibly disturbing the feature of interest through the welding, cutting, and cleaning processes, the in-situ method also ties up the FIB system, reducing throughput.

In the ex-situ method, a very fine probe is created by drawing a glass rod to form a sharp tip. The device 100 is removed from the FIB system and a mechanical translator is used to maneuver the probe into close proximity of one of the side portions 305 of the membrane 210. As the probe is brought close to the side portion 305, electrostatic forces between the glass of the probe and the membrane 210 cause the membrane to break free from the device 100, and in some instances causes the membrane 210 to jump to the probe. Unfortunately, in other instances the membrane 210 flies away from the probe.

Provided that the membrane 210 is successfully captured by the probe, the membrane 210 can then be maneuvered to a TEM support grid. The TEM support grid is a 3 mm diameter disk having a fine mesh of copper wires. A very thin film of holey carbon is deposited on the copper mesh. Ideally, the membrane 210 is placed on the holey carbon film such that the central portion 300 of the membrane 210 is aligned with one of the holes in the holey carbon. However, because the membrane 210 is held to the probe only by electrostatic forces, it is often difficult to position the membrane 210 precisely on the TEM support grid. While the ex-situ method is desirable over the in-situ method because it frees the FIB system for other work, and does not include the steps of welding the membrane 210 to the probe, cutting the membrane 210 from the probe, and cleaning excess platinum from the membrane 210, the ex-situ method suffers from low yield due to the unpredictability of the electrostatic forces on which it relies.

Accordingly, what is needed is a more reliable ex-situ method for producing TEM samples from devices.

SUMMARY

A manipulator for handling micron-scale samples comprises a probe, a probe holder, and a mechanical positioner. The probe includes a proximal end, a distal end, and an electrically conductive surface such as a metal coating. The distal end of the probe has a truncated conical shape with a generally flat face, and in some embodiments the face has a diameter along a minor axis of less than about 50 µm. The probe also includes a bore extending from the proximal end to the face. A diameter of the bore at the distal end, in some embodiments, is about 5 µm or less. The probe defines a longitudinal axis, the generally flat face defines a plane, and a normal axis of the plane, and in some embodiments the normal axis is angled with respect to the longitudinal axis. Also in some embodiments, the probe is a glass capillary tube that has been modified to have the features noted above.

The probe holder is engaged with the proximal end of the probe and includes a first inlet in fluid communication with the bore of the probe and with a source of sub-ambient pressure. In some embodiments, the probe holder further comprises a second inlet in fluid communication with the bore and with a source of ambient or super-ambient pressure. The mechanical positioner is configured to cause and control micron-scale movements of the probe holder.

A manipulator system for handling micron-scale samples comprises a manipulator as described above and a source of sub-ambient pressure coupled to a first inlet of the probe holder. The manipulator system can further comprise a source of ambient or super ambient pressure coupled to a second inlet in fluid communication with the bore.

A method for microscopy inspection comprises forming a free-standing membrane, positioning a probe proximate to the membrane, drawing a vacuum through a bore in the probe to draw the membrane to a generally flat face of a distal end of the probe, placing the membrane on a sample support such as a TEM support grid, and inspecting the membrane with a microscope. Forming the free-standing membrane can include focused ion beam milling. Positioning the probe can include translating a probe holder engaged with the probe. In some embodiments, placing the membrane on a sample support can include repositioning the probe such that the membrane is disposed proximate to the sample support, and discontinuing to draw the vacuum through the bore. In some of these embodiments the method further comprises introducing ambient or super-ambient pressure through the bore. Also, in some of these embodiments the method further comprises repositioning the probe such that the membrane touches the sample support.

A method of forming a probe for a manipulator for handling micron-scale samples comprises necking a capillary tube including a bore to form a closed and pointed end thereof, removing the closed end of the capillary tube, and coating the capillary tube with a conductive coating. The step of removing the closed end of the capillary tube provides the capillary tube with a distal end having a truncated conical shape with a generally flat face, the face having a diameter along a minor axis of less than about 50 µm, the bore of the capillary tube being exposed at the flat face. In some embodiments, removing the closed end of the capillary tube includes milling the closed end of the capillary tube with a focused ion beam. In some embodiments, coating the capillary tube includes sputter depositing a metal. Also in some embodiments, necking the capillary tube includes securing a first end of the capillary tube, applying a force to a second end of the capillary tube in a direction away from the first end, and heating a portion of the capillary tube between the two ends such that the capillary tube plastically deforms in response to the applied force.

BRIEF DESCRIPTION OF DRAWINGS

FIG. 12 is a front view of an apparatus for performing certain steps of the method of FIG. 11 according to an embodiment of the present invention.

FIG. 13 is a side view of the apparatus of FIG. 12 and including a partially necked capillary tube according to an embodiment of the present invention.

FIG. 14 is a side view of the apparatus of FIG. 12 and including a necked capillary tube according to an embodiment of the present invention.

FIG. 15 is a side view of the capillary tube of FIG. 14.

DETAILED DESCRIPTION

The present invention provides improvements for both in-situ and ex-situ preparation of micron-scale samples. A manipulator for handling micron-scale samples, according to an embodiment of the invention, comprises a probe including a bore and an electrically conductive surface. The electrically conductive surface dissipates static charges that might otherwise interact with the sample as the probe is brought into proximity to the sample. A vacuum drawn through the bore pulls the sample to the probe and secures the sample to the probe during subsequent handling. The disclosure also describes manipulator systems that include the manipulator, methods for microscopy inspection that employ at least the probe of the manipulator, and methods for making the probe.

Figure 4:
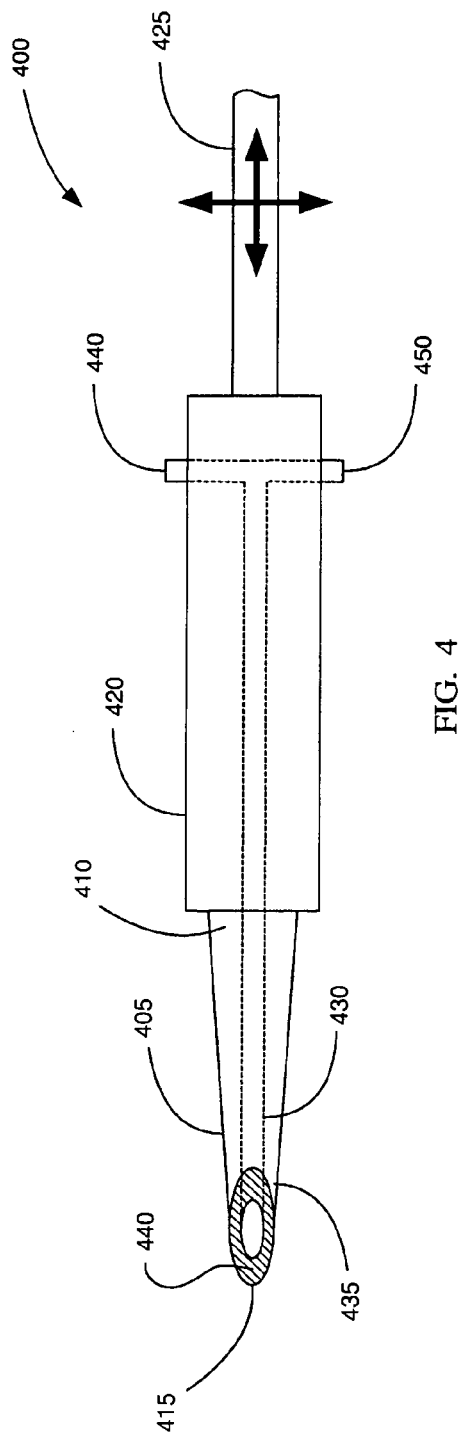
FIG. 4 is a bottom view of a manipulator according to an embodiment of the present invention.
Figure 5:
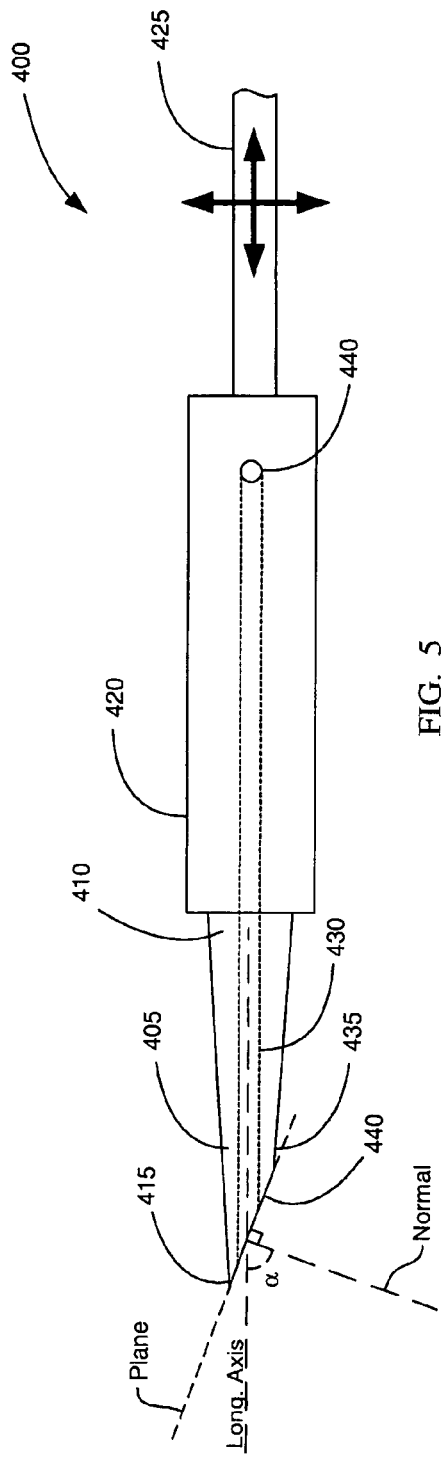
FIG. 5 is a side view of the manipulator of FIG. 4.

FIGS. 4 and 5 show bottom and side views, respectively, of a manipulator 400 for handling micron-scale samples according to an embodiment of the present invention. Micron-scale samples can include micron-scale devices and mechanical parts thereof, samples for microscopic analysis, and so forth. The manipulator 400 comprises a probe 405 having a proximal end 410 and a distal end 415, a probe holder 420 engaged with the proximal end 410 of the probe 405, and a mechanical positioner 425 configured to cause and control micron-scale movements of the probe holder 420. The probe 405 includes a bore 430 extending from the proximal end 410 to the distal end 415, and an electrically conductive surface 435. The probe holder 420 includes at least a first inlet 440 in fluid communication with the bore 430 and with a source of sub-ambient pressure (see FIG. 6), such as a vacuum pump or other device capable of maintaining a sub-ambient pressure.

In operation, the positioner 425 moves the probe holder 420 in order to position the probe 405 proximate to a micron-scale sample (not shown). A vacuum drawn through the bore 430 urges the sample to the distal end 415 and then secures the sample to the distal end 415. It will be understood that "drawing a vacuum" is used herein to mean lowering the air pressure within the bore 430 below the ambient air pressure. Drawing a vacuum through the bore 430 creates a sub-ambient pressure region around where the bore 430 is exposed at distal end 415. Air moving into the sub-ambient pressure region pushes the sample towards the distal end 415. It will likewise be understood that as used herein, the concept of the vacuum holding or securing the sample to the distal end 415 means that when the sample is covering the bore 430, the air pressure imbalance between the bore 430 and the ambient air pressure produces a force against the sample in the direction of the bore 430 that keeps the sample pressed against the distal end 415. Methods of using the manipulator 400 will be discussed in greater detail further herein.

As can be seen from FIGS. 4 and 5, the distal end 415 of the probe 405 has a truncated conical shape with a generally flat face 440. "Generally" flat is used herein to allow for variations such as rounding of edges, surface texturing, and so forth. As shown in FIG. 5, the face 440 defines a plane, and the probe 405 defines a longitudinal axis. In some embodiments, a normal axis to the plane defined by the face 440 is angled, by an angle, $\alpha$, with respect to the longitudinal axis defined by the probe 405.

In some embodiments the angle, $\alpha$, is zero meaning that the plane defined by the face 440 is perpendicular to the longitudinal axis of the probe 405. It will be appreciated that in these embodiments the face 440 is circular. In other embodiments the angle, $\alpha$, is in the range of 30° to 65°. In these embodiments the face 440 is oval with a minor (short) axis and a major (long) axis. It will be understood that in those embodiments in which the face 440 is circular the minor axis and the major axis are equal. Preferably, a diameter of the face 440 measured along the minor axis is less than about 50 μm.

The bore 430 of the probe 405 is exposed at the distal end 415 to create an opening in the face 440. In some embodiments, a diameter of the bore 430 measured at the distal end 415 is between about 1 μm and about 50 μm, and preferably about 5 μm or less. The probe 405 can be made, for example, from a low dielectric borosilicate glass. In some embodiments the dielectric constant can be in the range of about 4 to about 10. An exemplary borosilicate glass has a dielectric constant of 4.6 when measured at 1 MHz and 20° C. Methods for fabricating the probe 405 are described in greater detail, below.

As noted, the probe 405 also includes the electrically conductive surface 435. The surface 435 serves to keep static charges from accumulating on the probe 405. Such static build-up can undesirably repel or attract the sample, which can lower the reliability of methods for microscopy inspection that employ the manipulator 400, discussed in more detail below. Preferably, the probe holder 410 includes a path to an electrical ground in order to ground the probe 405. However, even without such a path to ground, the electrical conductivity of the surface 435 will serve to delocalize static and lessen the likelihood that static will interfere with sample manipulation. In some embodiments the electrically conductive surface 435 is a surface coating including a metal such as chromium.

The probe holder 420 engages the proximal end 410 of the probe 405. For example, the probe holder can include a recess for receiving the probe 405. The recess can include an O-ring for forming an air-tight seal around the circumference of the probe 405. However, any means can be used to secure the probe 405 to the probe holder 420. Preferably, the engagement means allows for the probe 405 to be readily exchanged with another.

In certain embodiments, the probe holder 420 serves to connect at least the sub-ambient pressure source to the bore 430 of the probe 405. Accordingly, in such embodiments the probe holder 420 also includes a bore or other conduit to provide fluid communication between the first inlet 440 and the bore 430 of the probe 405. In other embodiments the probe holder 420 is physically separate from the connection to the sub ambient pressure source. The probe holder 420 can also connect the bore 430 to a source of ambient or super-ambient pressure. In some of these embodiments the probe holder 420 also comprises a second inlet 450 in fluid communication with the bore 430 and with the source of ambient or super-ambient pressure.

It will be appreciated that the first and second inlets 440 and 450 can include valves. In these embodiments the amount of vacuum or gas introduced to the probe holder 420 can be regulated at the respective inlets 440, 450. Alternatively, inlets 440 and 450 can be simple connectors, and in these embodiments regulation can be performed along the line from the inlet 440, 450 to the respective source, or at the source.

In an exemplary embodiment, the probe holder 420 comprises a hollow 12 cm long metallic rod that is open at both ends. One end has a cap with a 1 mm diameter opening and a rubber adaptor. When the probe 405 is inserted into the cap, the rubber adaptor seals against the probe 405. The opposite end of the rod is connected with a flexible vacuum hose to a T-connector. The two arms of the T-connector each include a valve. One valve can be attached to a source of sub-ambient pressure, while the other valve can be either attached to a source of ambient or super-ambient pressure, or left exposed to the atmosphere.

The positioner 425 is shown in FIGS. 4 and 5 as being attached to an end of the probe holder 420 opposite to the probe 405. It will be understood, however, that the positioner 425 can secure the probe holder 420 in any practical manner. Likewise, in FIGS. 4 and 5 the positioner 425 is shown having two directions of motion. It will be appreciated, however, that in some embodiments of the invention the positioner 425 provides three directions of motion, and in further embodiments the positioner 425 also provides rotation about one or more axes.

In an exemplary embodiment, the positioner 425 comprises a coarse manipulation system, a fine manipulation system, and a stage having a clamp for securing the probe holder 420. In this embodiment the clamp secures the probe holder 420 near the center of the length of the probe holder 420, rather than at an end of the probe holder 420 as illustrated in FIGS. 4 and 5. Securing the probe holder 420 near its center of gravity reduces vibrations at the end of the probe 405. The manipulation systems may be capable of translating the stage in each of three orthogonal axes although the use of rotational stages is not inconsistent with the present invention. Coarse adjustment can be achieved by three coarse adjustment screws, while fine adjustment can be achieved by a oil hydraulic system having a three-axis joystick control and three flexible oil hydraulic lines, one for each of three axes. The entire positioner 425 attaches to an optical microscope base.

Figure 6:
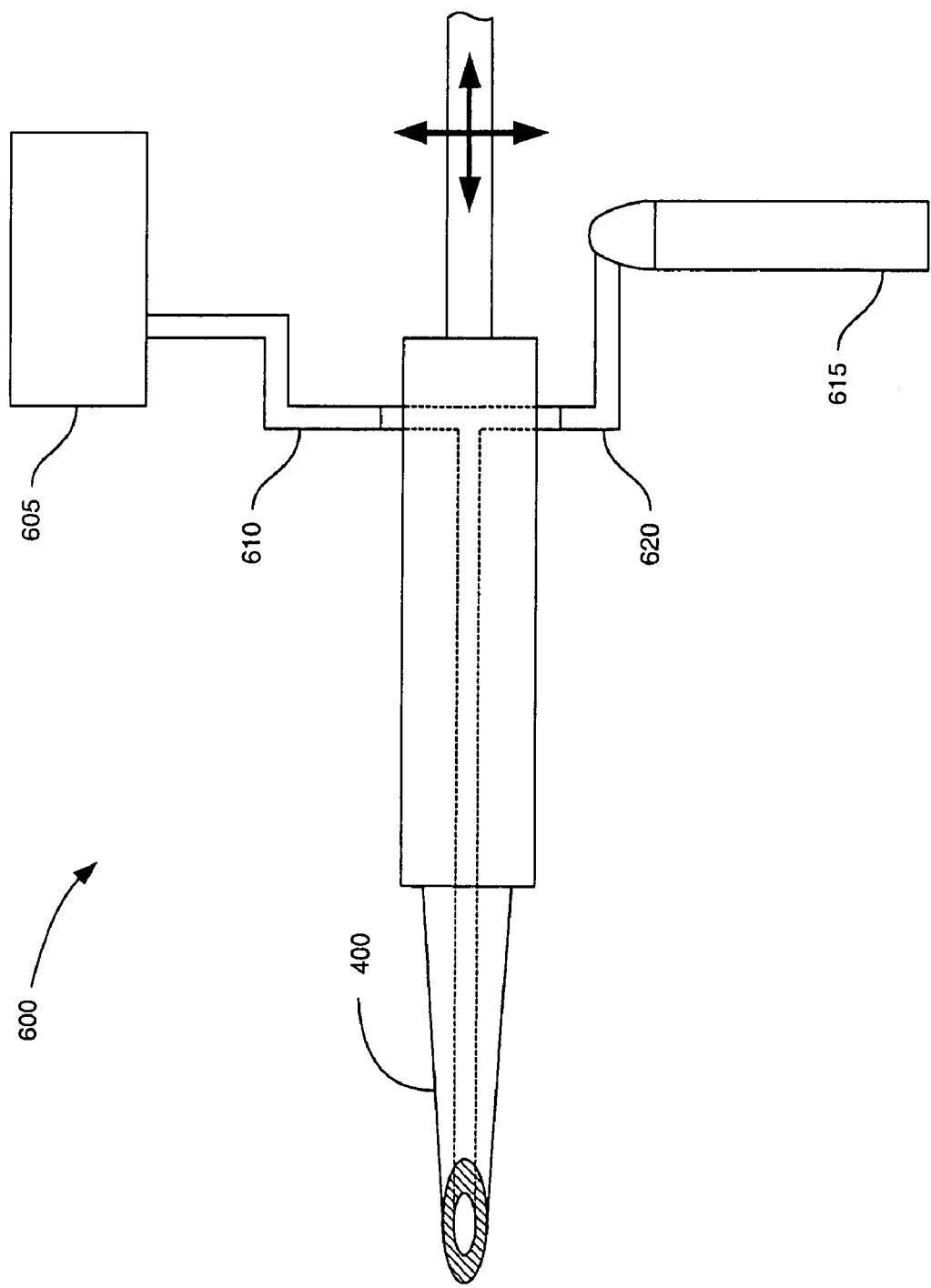
FIG. 6 is a bottom view of a manipulator system according to an embodiment of the present invention.

FIG. 6 illustrates a manipulator system 600 according to an embodiment of the present invention. The manipulator system 600 includes a manipulator 400, as described above, and at least a source 605 of sub-ambient pressure. A vacuum line 610 connects the source 605 to the first inlet 440. The manipulator system 600 can also include a source 615 of ambient or super-ambient pressure. A gas line 620 connects the source 615 to the second inlet 450. The source 615 can include compressed air or air at ambient pressure. The source 615 can also include other gases such as nitrogen, argon, helium, mixtures thereof, and so forth.

As noted above, regulation of the vacuum and gas can be achieved at the sources 605, 615, at the inlets 440, 450, or along the lines 610, 620. Preferably, the lines 610 and 620 are flexible and light weight so as not to restrict or impede the movement of the probe holder 420. It will be appreciated that separate inlets 440 and 450 are not required for the sources 605 and 615. For example, lines 610 and 620 can come together at a T-connector that is coupled to the first inlet 440. In these embodiments the regulation of the vacuum and gas can be achieved at the sources 605, 615, at the arms of the T-connector, or along the lines 610, 620 between the sources 605, 615 and the T-connector.

The manipulator system 600 can also comprise a microscope system (not shown) for observing the manipulator 400 during the positioning of the probe 405 relative to the sample. The manipulator system 600 can also comprise software or firmware (not shown) for performing part or all of the positioning of the manipulator 400. In some embodiments the manipulator system 600 is configured to work within a FIB milling system.

Figure 7:
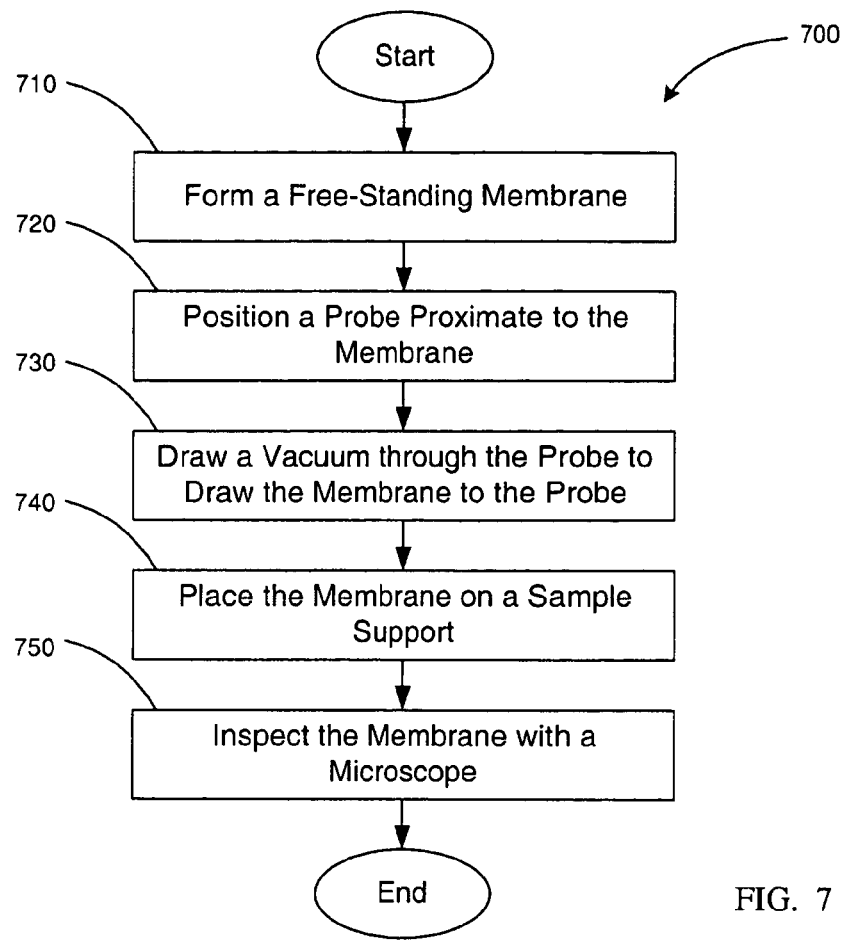
FIG. 7 is a flow-chart showing steps of a method for microscopy inspection according to an embodiment of the present invention.

FIG. 7 illustrates the steps of a method 700 for microscopy inspection according to an embodiment of the present invention. The method 700 includes a step 710 in which a free-standing membrane is formed, a step 720 in which a probe is positioned proximate to the membrane, a step 730 in which a vacuum is drawn through the probe to draw the membrane to the probe, a step 740 in which the membrane is placed on a sample support, and a step 750 in which the membrane is inspected by a microscope.

Figure 1:
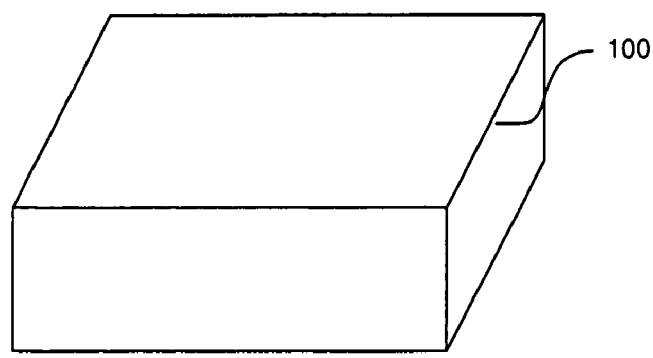
FIG. 1 is a perspective view of a device including a buried feature for inspection according to the prior art.
Figure 2:
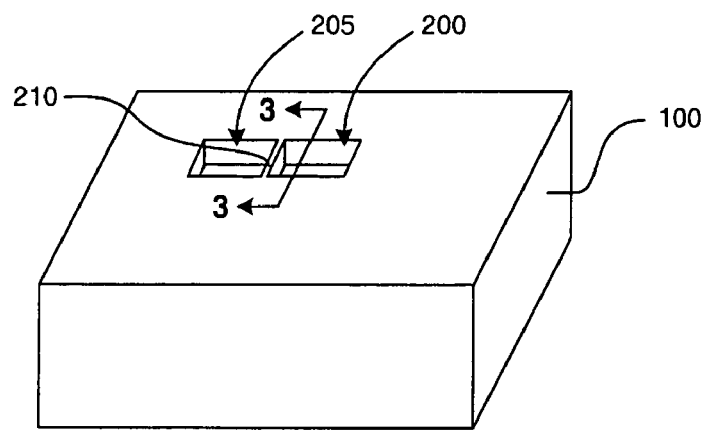
FIG. 2 is a perspective view of the device of FIG. 1 after a membrane including the feature has been prepared according to the prior art.
Figure 3:
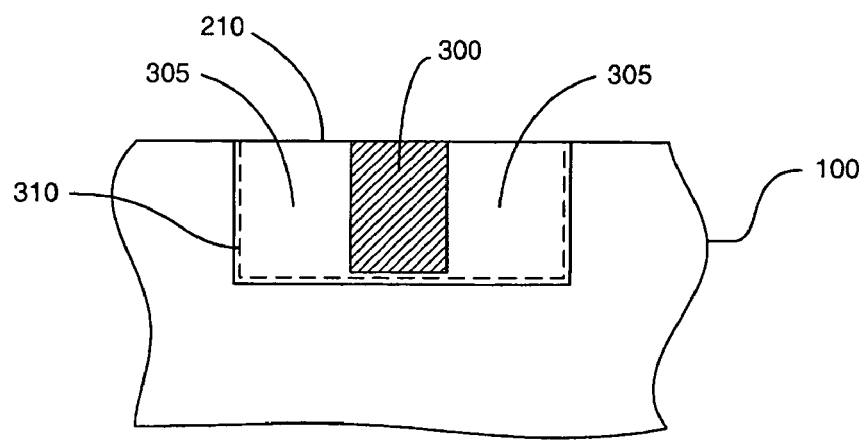
FIG. 3 is a view of the membrane of FIG. 2 from the perspective of 3—3 in FIG. 2.

In step 710 the free-standing membrane is formed. FIGS. 1–3 illustrate one embodiment for creating the free-standing membrane 210. As discussed above with reference to FIG. 2, FIB milling can be used to create pits 200 and 205 on either side of the feature of interest such that the membrane 210 containing the feature remains between the two pits 200 and 205. As shown in FIG. 3, the cut 310 around the perimeter of the membrane 210 allows the membrane 210 to be free-standing. As shown in FIG. 3, forming the free-standing membrane 210 can also include further thinning of the central portion 300 of the membrane 210. While FIB milling is one technique for creating the pits 200 and 205, thinning the central portion 300, and making the cut 310, other suitable techniques can be readily substituted for FIB milling.

Figure 8:
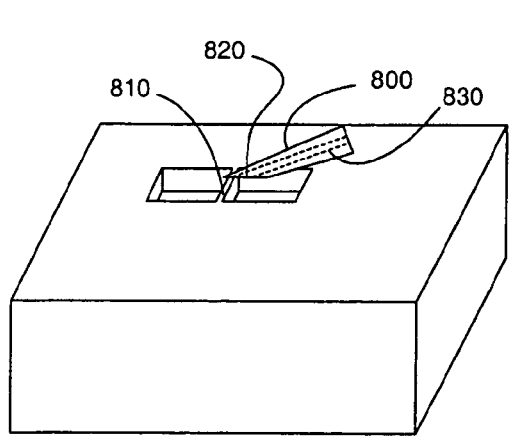
FIG. 8 is a perspective view of a probe of a manipulator disposed proximate to a free-standing membrane according to an embodiment of the present invention.

In step 720, as shown in FIG. 8, a probe 800 is positioned proximate to a membrane 810 such as membrane 210 (FIGS. 2 and 3). As illustrated, the probe 800 includes a distal end having a truncated conical shape with a generally flat face 820. In some embodiments the face 820 has a diameter along a minor axis of less than about 50 µm. The probe 800 also includes a bore 830 exposed at the face 820. Preferably, the probe 800 also includes an electrically conductive surface.

In step 720 the probe 800 is oriented such that the face 820 is positioned proximate to the membrane 810. In an embodiment of the present invention, positioning the face 820 proximate to the membrane 810 includes translating a probe holder 420 (FIGS. 2 and 3) engaged with the probe 800. Translating the probe holder 420 can be accomplished, for example, by a mechanical positioner 425 (FIGS. 2 and 3).

Figure 9:
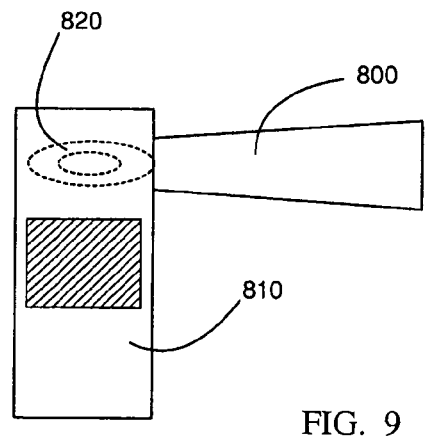
FIG. 9 is a bottom view of a probe of a manipulator holding a membrane according to an embodiment of the present invention.

In step 730 the vacuum is drawn through the bore 830 of the probe 800 to draw the membrane 810 to the probe 800. Once drawn to the probe 800, the membrane 810 is secured to the face 820 of the probe 800 by the vacuum. FIG. 9 shows a bottom view of the membrane 810 as secured to the face 820. To avoid damaging the feature of interest within the central portion 300 (FIG. 3), the face 820 is preferably positioned proximate to the side portion 305 (FIG. 3). In this way, the side portion 305 of the membrane 810 becomes secured to the face 820 as shown in FIG. 9.

It will be appreciated that the force drawing the membrane 810 towards the probe 800 depends upon the strength of the vacuum and the distance between the face 820 and the membrane. As the membrane 810 can be quite fragile, keeping the force to a minimum necessary to draw the membrane to the face 820 is desirable. One approach is to position the face 820 approximately 5 µm from the membrane 810, draw the vacuum through the bore 830, and then slowly move the probe 800 gradually closer to the membrane 810 until the membrane 810 is drawn to the face 820. In this approach step 730 is initiated before step 720 is completed.

An alternative is to draw the vacuum through the bore 830 after the probe 800 has been positioned in step 720. Then, in step 730, the vacuum level is slowly increased (meaning that the pressure within the bore 830 is slowly lowered) until the membrane 810 is drawn to the face 820. With reference to FIG. 6, the vacuum level in the bore 830 can be controlled, for example, by controlling the vacuum level at the first inlet 440 and the pressure at the second inlet 450.

Figure 10:
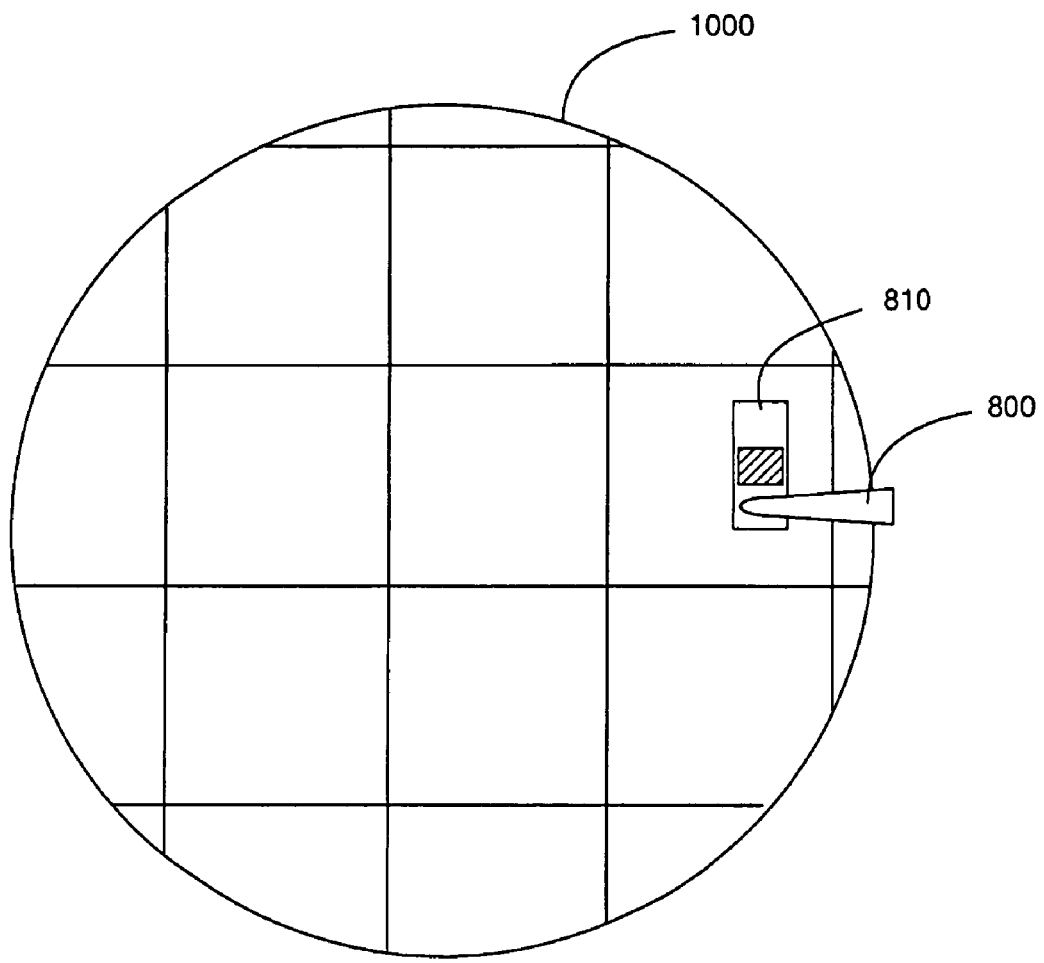
FIG. 10 is a top view of a probe of a manipulator holding a membrane proximate to a sample support according to an embodiment of the present invention.

In step 740, illustrated by FIG. 10, the membrane 810 is placed on a sample support 1000. Step 740 can include, for instance, repositioning the probe 800 is so that the membrane 810 is positioned proximate to the sample support 1000. FIG. 10 shows a top view of the probe 800 securing the membrane 810 above the sample support 1000. Although the sample support 1000 shown in FIG. 10 is a typical 3 mm TEM support grid, the sample support 1000 can also be an SEM sample stub or a mounting device for optical microscopy.

In an embodiment of the present invention, positioning the membrane 810 proximate to the sample support 1000 includes translating a probe holder 420 (FIGS. 2 and 3) engaged with the probe 800. Translating the probe holder 420 can be accomplished, for example, by a mechanical positioner 425 (FIGS. 2 and 3). In this step, a suitable spacing between the membrane 810 and the sample support 1000 after the membrane 810 has been positioned proximate to the sample support 1000 is 2 µm to 3 µm. It should be noted that repositioning the probe 800 so that the membrane 810 is positioned proximate to the sample support 1000 can include removing the probe 800 (still holding the membrane 810) from within a closed system, such as a FIB milling system. If the probe 800 is removed from the closed system, the method 700 is an ex-situ method, otherwise the method 700 is considered to be in-situ.

Step 740 can also include discontinuing to draw the vacuum through the bore 830. With reference to FIG. 10, discontinuing the vacuum allows the membrane 810 to be released from the probe 800 so that the membrane 810 can drop onto the sample support 1000. However, discontinuing the vacuum may not be enough to release the membrane 810 from the probe 800 because the pressure in the bore 830 may remain lower than the ambient pressure. Accordingly, the probe 800 can be further repositioned in step 740 such that the membrane 810 touches the sample support 1000. Touching the membrane 810 to the sample support 1000 can be sufficient to release the membrane 810 from the probe 800. Repositioning the probe 800 to touch the membrane 810 to the sample support 1000 can be performed before, during, or after the vacuum is discontinued.

In some embodiments merely discontinuing the vacuum and touching the membrane 810 to the sample support 1000 will not be sufficient to release the membrane 810 from the probe 800. In these embodiments, in step 740 ambient or super-ambient pressure is introduced into the bore 830 of the probe 800. Ambient pressure can be introduced, for example, by opening a valve connected to the second inlet 450 to allow air to enter the bore 830. Here, the valve is open to the atmosphere rather than a particular source. Ambient or super-ambient pressure can also be introduced by opening a valve between the second inlet 450 and the source 615 of ambient or super-ambient pressure (FIG. 6). In some instances, where the membrane 810 tends to stick to the probe 800, super-ambient pressure in the bore 830 can help to release the membrane 810 from the probe 800.

In step 750 the membrane is inspected with a microscope (not shown). The microscope can be an electron microscope or an optical microscope. Suitable electron microscopes include SEMs and TEMs. It will be understood, however, that the microscope can be any inspection tool. Still, the invention has a particular advantage when applied to TEM microscopy because of the special fragility of the very thin TEM samples.

Figure 11:
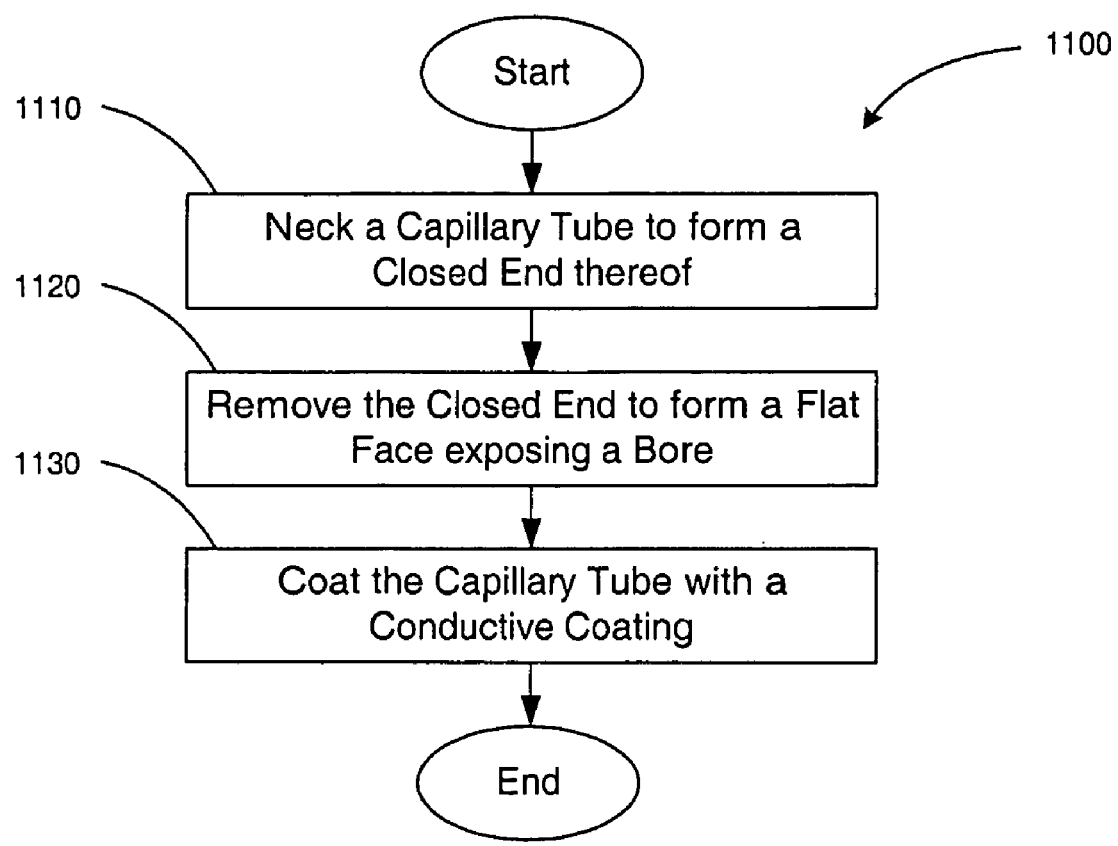
FIG. 11 is a flow-chart showing steps of a method of forming a probe for a manipulator according to an embodiment of the present invention.

FIG. 11 illustrates the steps of a method 1100 of forming a probe for a manipulator for handling microscopy samples according to an embodiment of the present invention. The method 1100 includes a step 1110 in which a capillary tube is necked to form a closed and pointed end thereof, a step 1120 in which the closed end of the capillary tube is removed to provide the capillary tube with a distal end having a truncated conical shape with a generally flat face, and a step 1130 in which a conductive coating is applied to the capillary tube.

FIGS. 12 and 13 show front and side views, respectively, of an apparatus 1200 for carrying out certain steps of the method 1100. The apparatus 1200 includes a clamp 1205 and a heater 1210 formed in the shape of a ring so as to be able to heat an interior space thereof. The clamp 1205, or similar securing device, secures a capillary tube 1215 such that the capillary tube 1215 passes through the interior space of the heater 1210, as shown in FIGS. 12 and 13. In an embodiment of the invention, the capillary tube 1215 has a diameter of about 1 mm and is made from borosilicate glass.

In step 1110 of the method 1100, the capillary tube 1215 is necked to form a pointed end 1500 thereof that may be closed as shown by FIGS. 13–15. In an embodiment of the method 1100, as shown in FIG. 13, step 1110 includes securing a first end 1300 of the capillary tube 1215, applying a force, F, to a second end 1305 of the capillary tube 1215, and heating a portion of the capillary tube 1215 between the two ends 1300, 1305. In this embodiment, the force, F, is applied in a direction away from the first end 1300. Also in this embodiment, heating the portion of the capillary tube 1215 causes the capillary tube 1215 to plastically deform in response to the applied force, F. The plastic deformation of the capillary tube 1215 in FIG. 13 is illustrated by the necking of a bore 1310 of the capillary tube 1215 within the heater 1210. In an embodiment of the method 1100, the force, F, is applied by a weight (not shown) secured to the second end 1305. The weight can be attached, for example, to a vertical track (not shown) on the apparatus 1200 so that a direction of the track defines the direction of the force, F.

FIG. 14 illustrates the capillary tube 1215 still secured by the clamp 1205 after the capillary 1215 tube has been necked. A bottom portion of the capillary tube 1215, including the second end 1305, ultimately falls away in the process illustrated by FIG. 13. FIG. 15 shows the capillary tube 1215 with the closed and pointed end 1500 after having been removed from the apparatus 1200.

Figure 16:
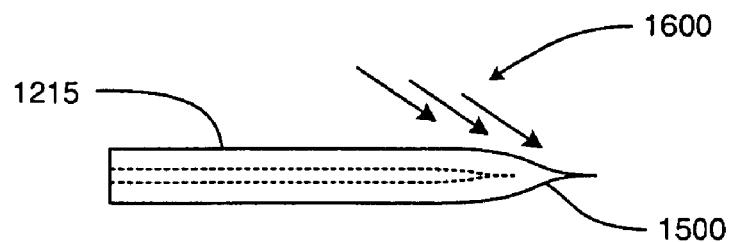
FIG. 16 is a side view of the capillary tube of FIG. 15 being subjected to a process for removing a portion of a closed end thereof, according to an embodiment of the present invention.
Figure 17:
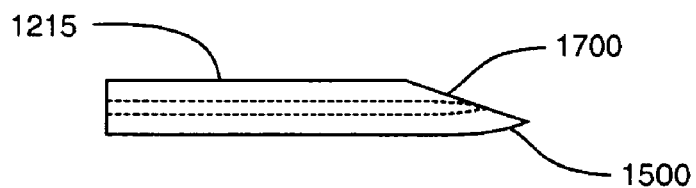
FIG. 17 is a side view of the capillary tube of FIG. 16 after the portion of the closed end has been removed, according to an embodiment of the present invention.

In step 1120 of the method 1100 the closed (or nearly closed) end 1500 of the capillary tube 1215 is removed to form a truncated conical shape with a generally flat face and to expose the bore 1300 of the capillary tube 1215 at the flat face. An exemplary process for achieving step 1120 is shown in FIGS. 16 and 17. In FIG. 16 the capillary tube 1215 is milled, such as by ion milling, with a beam of ions 1600. The capillary tube 1215, after the closed end 1500 is removed, is shown in FIG. 17. The beam of ions 1600, in some embodiments, is directed towards the closed end 1500 at an angle to a longitudinal axis (not shown) of the capillary tube 1215 to create a face 1700 having a normal axis (not shown) angled with respect to the longitudinal axis of the capillary tube 1215. Milling the closed end 1500 can be performed, for example, in a FIB system.

Figure 18:
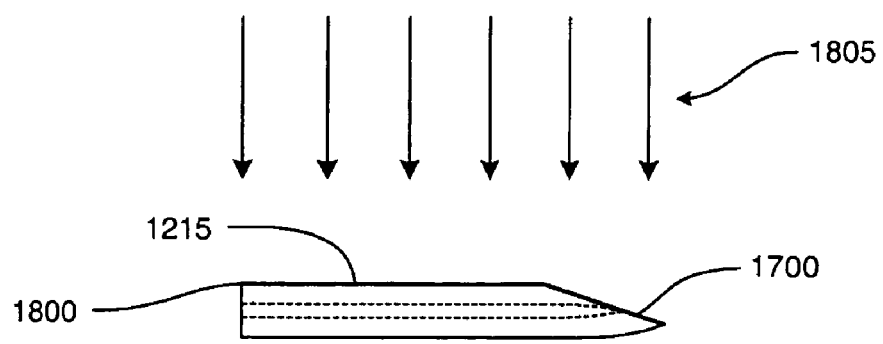
FIG. 18 is a side view of the capillary tube of FIG. 17 being subjected to a process for coating the capillary tube with a conductive coating according to an embodiment of the present invention.

In step 1130 of the method 1100 a conductive coating 1800 is applied to the capillary tube 1215, as shown in FIG. 18. In an embodiment of the present invention, coating the capillary tube 1215 includes sputter depositing a metal 1805, such as chromium. As shown in FIG. 18, sputter depositing the metal 1805 coats only the exposed side of the capillary tube 1215. It is preferable, therefore, to orient the capillary tube 1215 in the sputtering chamber (not shown) so that the face 1700 is coated. More preferably, the capillary tube 1215 is rotated during the coating process to obtain a conductive coating over the entire exposed surface.

In the foregoing specification, the present invention is described with reference to specific embodiments thereof, but those skilled in the art will recognize that the present invention is not limited thereto. Various features and aspects of the above-described present invention may be used individually or jointly. Further, the present invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A manipulator for handling micron-scale samples, the manipulator comprising:
   a probe including
      an electrically conductive surface,
      a proximal end and a distal end, the distal end having a truncated conical shape with a generally flat face, the face having a diameter along a minor axis of less than about 50 µm, and
      a bore extending from the proximal end to the face;
   a probe holder engaged with the proximal end of the probe and including a first inlet in fluid communication with the bore and with a source of sub-ambient pressure; and
   a mechanical positioner configured to cause and control micron-scale movements of the probe holder.

2. The manipulator of claim 1 wherein the probe holder further comprises a second inlet in fluid communication with the bore and with a source of ambient or super-ambient pressure.

3. The manipulator of claim 1 wherein the probe comprises a glass capillary tube.

4. The manipulator of claim 3 wherein the glass capillary tube comprises glass having a dielectric constant less than 10.

5. The manipulator of claim 1 wherein the electrically conductive surface comprises a metal coating.

6. The manipulator of claim 5 wherein the metal coating includes chromium.

7. The manipulator of claim 1 wherein the probe defines a longitudinal axis, the generally flat face defines a plane, and a normal axis of the plane is angled with respect to the longitudinal axis.

8. The manipulator of claim 7 wherein the normal axis of the plane is angled with respect to the longitudinal axis by an angle in the range of 30° to 65°.

9. The manipulator of claim 1 wherein a diameter of the bore at the distal end is about 5 µm or less.

10. The manipulator of claim 1 wherein the probe holder includes a path to an electrical ground in order to ground the probe.

11. A manipulator system for handling micron-scale samples, the system comprising:
- a probe including
  - an electrically conductive surface,
  - a proximal end and a distal end, the distal end having a truncated conical shape with a generally flat face, the face having a diameter along a minor axis of less than about 50 µm, and
  - a bore extending from the proximal end to the face;
- a probe holder engaged with the proximal end of the probe and including a first inlet in fluid communication with the bore;
- a mechanical positioner configured to cause and control micron-scale movements of the probe holder; and
- a source of sub-ambient pressure coupled to the inlet.

12. The manipulator system of claim 11 further comprising a source of ambient or super ambient pressure coupled to a second inlet in fluid communication with the bore.

13. A method for microscopy inspection, comprising:
forming a free-standing membrane;
positioning a probe proximate to the membrane, the probe including
- an electrically conductive surface,
- a distal end having a truncated conical shape with a generally flat face, the face having a diameter along a minor axis of less than about 50 µm,
- a bore extending from the proximal end to the face, and
- a probe holder engaged with the proximal end of the probe and including a first inlet in fluid communication with the bore;

drawing a vacuum through the bore to draw the membrane to the face;
placing the membrane on a sample support; and
inspecting the membrane with a microscope.

14. The method of claim 13 wherein forming the free-standing membrane includes focused ion beam milling.

15. The method of claim 13 wherein positioning the probe includes translating a probe holder engaged with the probe.

16. The method of claim 13 wherein placing the membrane includes
repositioning the probe such that the membrane is disposed proximate to the sample support; and
discontinuing to draw the vacuum through the bore.

17. The method of claim 16 wherein the sample support is a TEM support grid.

18. The method of claim 16 further comprising introducing ambient or super-ambient pressure through the bore.

19. The method of claim 16 further comprising repositioning the probe such that the membrane touches the sample support.

20. The method of claim 13 wherein forming the free-standing membrane and placing the membrane on the sample support are performed within a focused ion beam milling system.

* * * * *